(12) United States Patent
Hayashi et al.

(10) Patent No.: US 11,302,092 B2
(45) Date of Patent: Apr. 12, 2022

(54) INSPECTION SUPPORT DEVICE, ENDOSCOPE DEVICE, INSPECTION SUPPORT METHOD, AND INSPECTION SUPPORT PROGRAM

(71) Applicant: FUJIFILM Corporation, Tokyo (JP)

(72) Inventors: Shinji Hayashi, Kanagawa (JP);
Masaaki Oosake, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/842,761

(22) Filed: Apr. 8, 2020

(65) Prior Publication Data
US 2020/0234070 A1 Jul. 23, 2020

Related U.S. Application Data

(63) Continuation of application No. PCT/JP2018/038754, filed on Oct. 18, 2018.

(30) Foreign Application Priority Data

Oct. 31, 2017 (JP) .............................. JP2017-210379

(51) Int. Cl.
*A61B 1/00* (2006.01)
*G06V 10/22* (2022.01)
(Continued)

(52) U.S. Cl.
CPC ........ *G06V 10/235* (2022.01); *A61B 1/00045* (2013.01); *A61B 1/045* (2013.01);
(Continued)

(58) Field of Classification Search
CPC .............. G06K 9/2081; G06K 9/2054; G06K 2209/05; A61B 1/00045; A61B 1/045;
(Continued)

(56) References Cited

U.S. PATENT DOCUMENTS 9,220,468 B2 * 12/2015 Kitamura ............... A61B 34/20
9,521,330 B2   12/2016 Kuriyama
(Continued)

FOREIGN PATENT DOCUMENTS

JP   2001258802   9/2001
JP   2001258820   9/2001
(Continued)

OTHER PUBLICATIONS

"Office Action of Japan Counterpart Application", dated Nov. 4, 2020, with English translation thereof, p. 1-p. 8.
(Continued)

*Primary Examiner* — Howard D Brown, Jr.
(74) *Attorney, Agent, or Firm* — JCIPRNET

(57) ABSTRACT

The system control unit functions as a captured image data acquisition unit that acquires captured image data obtained by imaging the inside of a subject with an endoscope; a visual-line detection unit 44B that detects a visual line directed to a display device that displays a captured image based on the captured image data; a processing unit that performs recognition processing for performing detection of a lesion site from the captured image data and identification of the detected lesion site on the captured image data; and a display control unit for causing the display device to display a result of the recognition processing by the processing unit. The processing unit controls the content of the recognition processing on the captured image data on the basis of the visual line detected by the visual-line detection unit.

18 Claims, 13 Drawing Sheets

(51) Int. Cl.
*A61B 1/045* (2006.01)
*G06T 7/00* (2017.01)

(52) U.S. Cl.
CPC .. *G06T 7/0012* (2013.01); *G06T 2207/10068* (2013.01); *G06T 2207/30096* (2013.01)

(58) Field of Classification Search
CPC ............ A61B 1/00039; A61B 1/00009; A61B 1/0005; G06T 7/0012; G06T 2207/10068; G06T 2207/30096; H04N 7/183; G02B 23/24
See application file for complete search history.

(56) References Cited

U.S. PATENT DOCUMENTS

| | | | | |
|---|---|---|---|---|
| 10,653,295 | B2 * | 5/2020 | Ebata | A61B 5/1459 |
| 10,863,893 | B2 * | 12/2020 | Imaizumi | A61B 1/00009 |
| 2012/0069166 | A1 | 3/2012 | Kunz et al. | |
| 2015/0077529 | A1 * | 3/2015 | Hatta | H04N 13/128 348/54 |
| 2016/0296106 | A1 | 10/2016 | Shoji | |
| 2017/0168297 | A1 * | 6/2017 | Morimoto | G02B 27/017 |
| 2017/0172381 | A1 * | 6/2017 | Morimoto | G06F 3/1454 |
| 2018/0049632 | A1 | 2/2018 | Shida | |
| 2018/0228347 | A1 | 8/2018 | Yamamoto | |
| 2018/0253839 | A1 * | 9/2018 | Zur | G06T 7/0012 |
| 2018/0344138 | A1 | 12/2018 | Kudo | |

FOREIGN PATENT DOCUMENTS

| | | |
|---|---|---|
| JP | 2005034211 | 2/2005 |
| JP | 2012115554 | 6/2012 |
| JP | 2012518504 | 8/2012 |
| JP | 2014094157 | 5/2014 |
| JP | 2017070636 | 4/2017 |
| JP | 2017153978 | 9/2017 |
| WO | 2013187116 | 12/2013 |
| WO | 2016092941 | 6/2016 |
| WO | 2016117277 | 7/2016 |
| WO | 2016170604 | 10/2016 |
| WO | 2017057574 | 4/2017 |
| WO | 2017081976 | 5/2017 |
| WO | 2017104233 | 6/2017 |
| WO | 2017183353 | 10/2017 |

OTHER PUBLICATIONS

"Search Report of Europe Counterpart Application", dated Oct. 9, 2020, p. 1-p. 7.

"International Search Report (Form PCT/ISA/210) of PCT/JP2018/038754," dated Jan. 15, 2019, with English translation thereof, pp. 1-5.

"Written Opinion of the International Searching Authority (Form PCT/ISA/237) of PCT/JP2018/038754," dated Jan. 15, 2019, with English translation thereof, pp. 1-7.

"Office Action of Japan Counterpart Application", dated Apr. 13, 2021, with English translation thereof, pp. 1-8.

* cited by examiner

INSPECTION SUPPORT DEVICE, ENDOSCOPE DEVICE, INSPECTION SUPPORT METHOD, AND INSPECTION SUPPORT PROGRAM

CROSS-REFERENCE TO RELATED APPLICATIONS

This application is a Continuation of PCT International Application No. PCT/JP2018/038754 filed on Oct. 18, 2018, which claims priority under 35 U.S.C § 119(a) to Japanese Patent Application No. 2017-210379 filed on Oct. 31, 2017. Each of the above application(s) is hereby expressly incorporated by reference, in its entirety, into the present application.

BACKGROUND OF THE INVENTION

1. Field of the Invention

The present invention relates to an inspection support device, an endoscope device, an inspection support method, and a non-transitory computer readable recording medium storing an inspection support program.

2. Description of the Related Art

With the development of medical devices such as computed tomography (CT), magnetic resonance imaging (MM), a virtual slide scanner for capturing a pathological specimen, or an endoscope device, a large amount of digitalized high-definition medical images can be acquired.

In recent years, picture archiving and communication systems (PACS) for saving medical images have spread, and these images are sequentially stored together with the doctor's diagnostic findings. As such digitization of the medical images and accumulation of cases progress, it has become possible to detect or identify a lesion using a computer as described in, for example, JP2014-094157A, JP2005-034211A, and JP2001-258820A.

JP2014-094157A describes a system in which, in a case where a user specifies a region of interest on a medical image, a detailed analysis is executed on the image within the region of interest, and an analysis result is displayed.

JP2005-034211A describes a system that extracts a lesion candidate region from a medical image and identifies a lesion on the extracted lesion candidate region, using a recognition model generated by machine learning.

JP2001-258820A describes a system that analyzes a captured image captured by an endoscope to detect a lesion site, and overlappingly displays the detected lesion site on the captured image. In this system, it is possible to perform the above analysis only on a region of the captured image to which an attention is paid by an observer.

SUMMARY OF THE INVENTION

In inspection using an endoscope device among the above-described medical devices, it is necessary to determine the presence or absence of a lesion site and to resect the lesion site while checking the captured image displayed on the display device in a state where an insertion part of the endoscope inserted into the body of a subject. For this reason, in the inspection using the endoscope device, it is necessary to perform the processing of detecting or identifying a lesion using a computer in real time during the inspection.

Such real-time processing imposes a heavy processing load on the computer. JP2014-094157A and JP2005-034211A describe a technique of executing analysis only on a specific region of a medical image, but assumes that the image data saved by the inspection or the like is analyzed after the inspection, and does not assume a case where a lesion is detected or identified in real time.

JP2001-258820A describes that at the time of inspection using an endoscope, analysis is performed only on a region to which an attention is paid on a captured image. However, no consideration has been given to how to select this region.

It is necessary to operate the endoscope using both hands, and at the time of the inspection, the operator is in a state where both hands closed. For this reason, in the captured image displayed in real time, how to determine a region where the processing of detection or identification of a lesion by the computer is needed is important in securing the accuracy and efficiency of the inspection.

The invention has been made in view of the above circumstances, and an object thereof is to provide an inspection support device, an endoscope device, an inspection support method, and an inspection support program that can make both the accuracy and efficiency of the inspection using the endoscope compatible.

An inspection support device of the invention comprises a captured image data acquisition unit that acquires captured image data obtained by imaging the inside of a subject with an endoscope; a visual-line detection unit that detects a visual line directed to a display device that displays a captured image based on the captured image data; a processing unit that performs processing for performing at least detection of the detection of a lesion site from the captured image data and identification of the detected lesion site on the captured image data; and a display control unit that causes the display device to display a result of the processing by the processing unit, wherein the processing unit controls a content of the processing on the captured image data on the basis of the visual line detected by the visual-line detection unit.

An endoscope device of the invention comprises the above inspection support device; and the endoscope.

An inspection support method of the invention comprises a captured image data acquisition step of acquiring captured image data obtained by imaging the inside of a subject with an endoscope; a visual-line detection step of detecting a visual line directed to a display device that displays a captured image based on the captured image data; a processing step of performing processing for performing at least a detection of a lesion site from the captured image data out of the detection of the lesion site and identification of the detected lesion site on the captured image data; and a display control step of causing the display device to display a result of the processing by the processing step, wherein in the processing step, a content of the processing on the captured image data is controlled on the basis of the visual line detected by the visual-line detection step.

A non-transitory computer readable recording medium storing an inspection support program of the invention causes a computer to execute a captured image data acquisition step of acquiring captured image data obtained by imaging the inside of a subject with an endoscope; a visual-line detection step of detecting a visual line directed to a display device that displays a captured image based on the captured image data; a processing step of performing processing for performing at least a detection of a lesion site from the captured image data out of the detection of the lesion site and identification of the detected lesion site on the captured image data; and a display control step of causing the display device to display a result of the processing by the processing step, wherein in the processing step, a content of the processing on the captured image data is controlled on the basis of the visual line detected by the visual-line detection step.

According to the invention, it is possible to provide the inspection support device, the endoscope device, the inspection support method, and the non-transitory computer readable recording medium storing the inspection support program that can make both the accuracy and efficiency of the inspection using the endoscope compatible.

DESCRIPTION OF THE PREFERRED EMBODIMENTS

Hereinafter, embodiments of the invention will be described with reference to the drawings.

Figure 1:
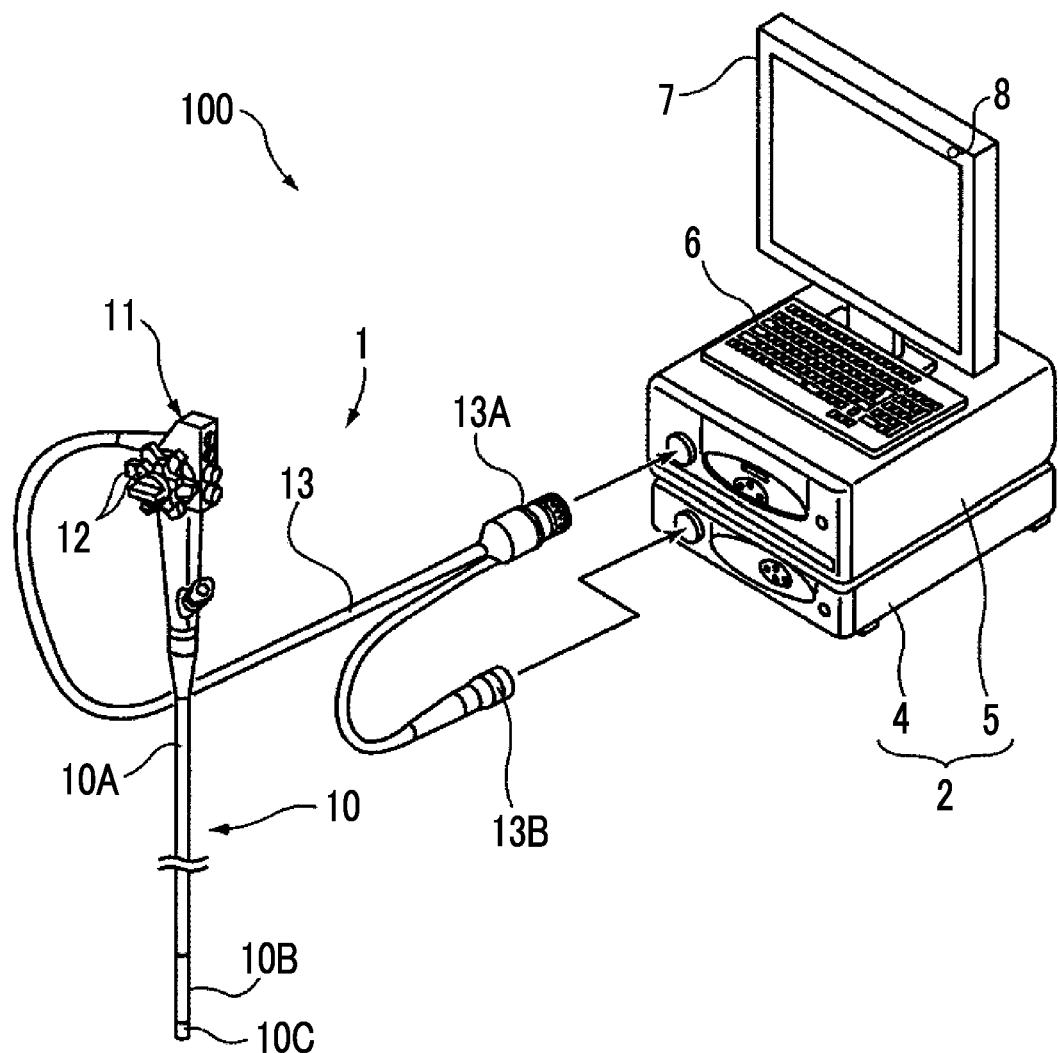
FIG. 1 is a view illustrating a schematic configuration of an endoscope device 100 that is an embodiment of the invention.

FIG. 1 is a view illustrating a schematic configuration of an endoscope device 100 that is an embodiment of the invention.

As illustrated in FIG. 1, the endoscope device 100 comprises an endoscope 1, and a body part 2 including a control device 4 and a light source device 5 to which the endoscope 1 is connected.

A display device 7 that displays a captured image or the like obtained by imaging the inside of a subject by the endoscope 1, an imaging device 8 installed near the display device 7, and an input unit 6, which is an interface for inputting various kinds of information to the control device 4, are connected to the control device 4. The control device 4 controls the endoscope 1, the light source device 5, the display device 7, and the imaging device 8.

The display device 7 has a display surface on which display pixels are two-dimensionally arranged, and pixel data constituting image data is drawn on each display pixel on the display surface, thereby performing display of an image based on the image data.

The imaging device 8 is provided to detect the visual line of an observer who observes an image displayed on the display surface of the display device 7, and is disposed so as to be able to capture an image in front of the display surface. A visual line detection image data obtained by imaging the subject with the imaging device 8 is transmitted to the control device 4.

The endoscope 1 comprises an insertion part 10 that is a tubular member extending in one direction and is inserted into the subject, an operating part 11 that is provided at a proximal end part of the insertion part 10 and is provided with operating members for performing an observation mode switching operation, an imaging and recording operation, a forceps operation, an air and water supply operation, a suction operation, and the like, an angle knob 12 provided adjacent to the operating part 11, and a universal cord 13 including connector parts 13A and 13B that attachably and detachably connect the endoscope 1 to the light source device 5 and the control device 4, respectively.

In addition, although omitted in FIG. 1, various channels, such as a forceps hole for inserting forceps for sampling a living tissue, such as cells or polyps, an air and water supply channel, and a suction channel, are provided inside the operating part 11 and the insertion part 10.

The insertion part 10 is constituted of a flexible part 10A that has flexibility, a bending part 10B provided at a distal end of the flexible part 10A, and a hard distal end part 10C provided at a distal end of the bending part 10B.

The bending part 10B is configured to be bendable by the rotational movement operation of the angle knob 12. Depending on regions of the subject in which the endoscope 1 is used, the bending part 10B can be bent in an optional direction and at an optional angle and the distal end part 10C can be directed in a desired direction.

Figure 2:
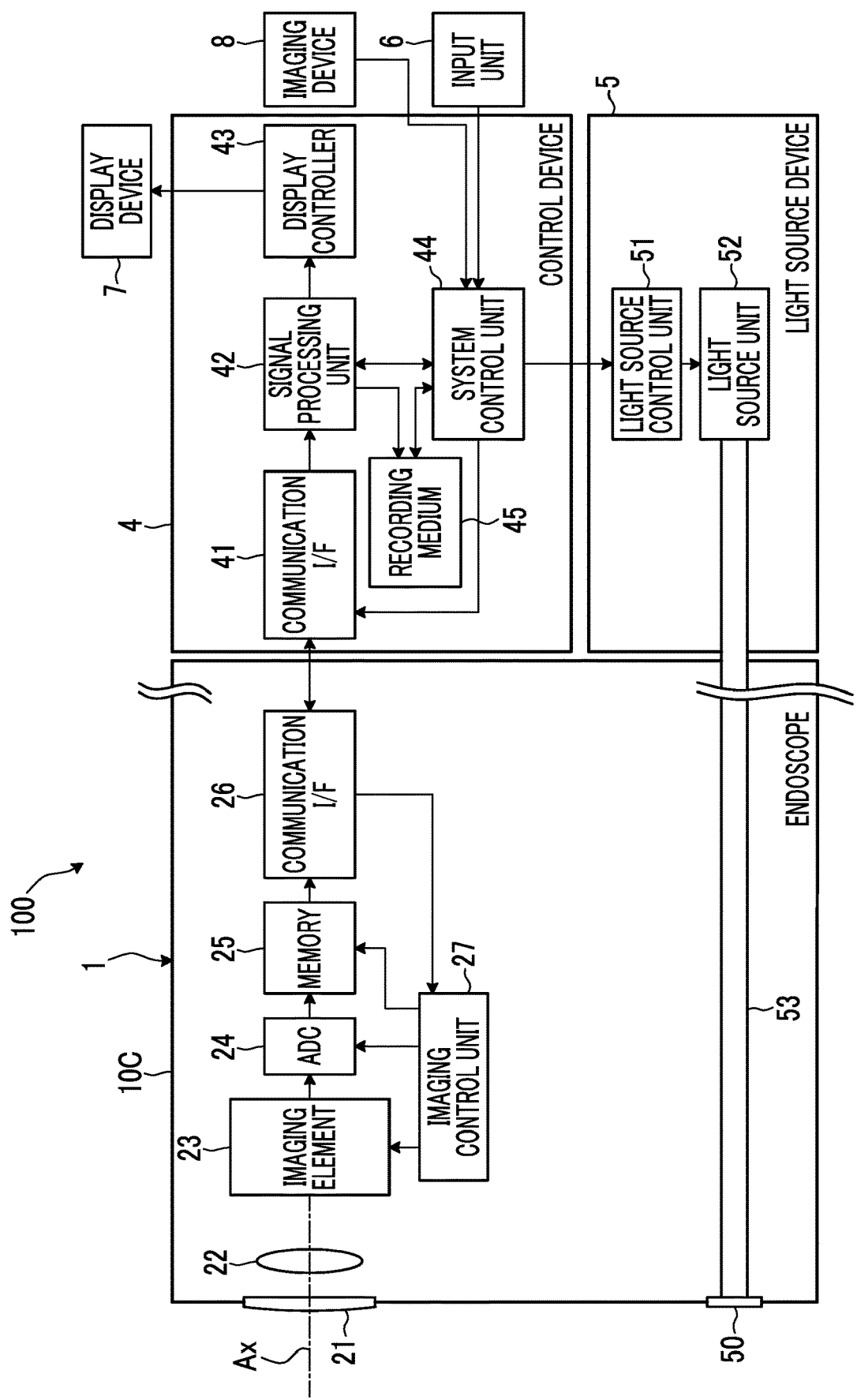
FIG. 2 is a schematic view illustrating an internal configuration of the endoscope device 100 illustrated in FIG. 1.

FIG. 2 is a schematic view illustrating an internal configuration of the endoscope device 100 illustrated in FIG. 1.

The light source device 5 comprises a light source control unit 51 and a light source unit 52.

The light source unit 52 generates illumination light for irradiating the subject. The illumination light emitted from the light source unit 52 enters a light guide 53 built in the universal cord 13, and is emitted to the subject through the illumination lens 50 provided at the distal end part 10C of the insertion part 10.

A white light source that emits white light, a plurality of light sources including the white light source and a light source (for example, a blue light source that emits blue light) that emits other color light, or the like is used as the light source unit 52. A plurality of illumination lenses 50 may be provided in conformity with the type of light emitted from the light source unit 52 on the distal end surface of the distal end part 10C.

The light source control unit 51 is connected to a system control unit 44 of the control device 4. The light source control unit 51 controls the light source unit 52 on the basis of a command from the system control unit 44.

The distal end part 10C of the endoscope 1 is provided with an imaging optical system including an objective lens 21 and a lens group 22, an imaging element 23 that images the subject through the imaging optical system, an analog/digital converter circuit (ADC) 24, a memory 25, such as a random access memory (RAM), a communication interface (I/F) 26, an imaging control unit 27, and the light guide 53 for guiding the illumination light emitted from the light source unit 52 to the illumination lens 50.

The light guide 53 extends from the distal end part 10C to the connector part 13A of the universal cord 13. The illumination light emitted from the light source unit 52 of the light source device 5 is allowed to enter the light guide 53 in a state where the connector part 13A of the universal cord 13 is connected to the light source device 5.

As the imaging element 23, a charge coupled device (CCD) image sensor or a complementary metal oxide semiconductor (CMOS) image sensor is used.

The imaging element 23 has a light-receiving surface on which a plurality of pixels are two-dimensionally arranged, converts an optical image formed on the light-receiving surface by the above imaging optical system into an electrical signal (imaging signal) in each pixel, and outputs the converted electrical signal to the ADC 24. As the imaging element 23, for example, one on which color filters, such as an elementary color or a complementary color, are mounted, is used. A set of the imaging signals output from the respective pixels of the light-receiving surface of the imaging element 23 is referred to as captured image signals.

In addition, in a case where one in which the spectrum of the white light emitted from the white light source is divided in a time-division manner by a plurality of color filters to generate the illumination light is used as the light source unit 52, one on which no color filter is mounted may be used as the imaging element 23.

The imaging element 23 may be disposed at the distal end part 10C in a state where the light-receiving surface is perpendicular to an optical axis Ax of the objective lens 21, or may be disposed at the distal end part 10C in a state where the light-receiving surface is parallel to the optical axis Ax of the objective lens 21.

The imaging optical system provided in the endoscope 1 is constituted of optical members (including the above lens group 22), such as a lens and a prism, which are present on an optical path of the light from the subject between the imaging element 23 and the objective lens 21, and the objective lens 21. There is also a case where the imaging optical system is constituted of only the objective lens 21.

The ADC 24 converts the imaging signal output from the imaging element 23 into a digital signal having a predetermined number of bits.

The memory 25 temporarily records the imaging signal digitally converted by the ADC 24.

The communication I/F 26 is connected to a communication interface (I/F) 41 of the control device 4. The communication I/F 26 transmits the imaging signal recorded in the memory 25 to the control device 4 through a signal line within the universal cord 13.

The imaging control unit 27 is connected to the system control unit 44 of the control device 4 via the communication I/F 26. The imaging control unit 27 controls the imaging element 23, the ADC 24, and the memory 25 on the basis of a command from the system control unit 44 to be received by the communication I/F 26.

The control device 4 comprises the communication I/F 41 connected to the communication I/F 26 of the endoscope 1 by the universal cord 13, a signal processing unit 42, a display controller 43, the system control unit 44, and a recording medium 45.

The communication I/F 41 receives the imaging signal transmitted from the communication I/F 26 of the endoscope 1 and transmits the imaging signal to the signal processing unit 42.

The signal processing unit 42 has a memory for temporarily recording the imaging signal received from the communication I/F 41 built therein, and processes captured image signals (image processing, such as demosaicing processing or gamma-correction processing) that are a set of the imaging signals recorded in the memory to generate captured image data in such a format that recognition processing to be described below is allowed. The captured image data generated by the signal processing unit 42 is recorded on the recording medium 45, such as a hard disk or a flash memory.

The display controller 43 causes the display device 7 to display a captured image based on the captured image data generated by the signal processing unit 42. The coordinates of each pixel data constituting the captured image data generated by the signal processing unit 42 are managed in association with the coordinates of any of the display pixels constituting the di splay surface of the di splay device 7.

The system control unit 44 controls the respective units of the control device 4, and sends commands to the imaging control unit 27 of the endoscope 1 and the light source control unit 51 of the light source device 5, and integrally controls the entire endoscope device 100.

The system control unit 44 performs the control of the imaging element 23 via the imaging control unit 27. Additionally, the system control unit 44 performs the control of the light source unit 52 via the light source control unit 51.

The system control unit 44 includes various processors that execute a program to perform processing, a random access memory (RAM), and a read only memory (ROM).

The various processors include a central processing unit (CPU) that is a general-purpose processor that executes a program to perform various kinds of processing, a programmable logic device (PLD), which is a processor capable of changing a circuit configuration after manufacture, such as a field programmable gate array (FPGA), or an exclusive electric circuit, which is a processor having a circuit configuration exclusively designed to execute specific processing, such as an application specific integrated circuit (ASIC).

The structure of these various processors is, more specifically, an electric circuit in which circuit elements, such as semiconductor elements, are combined together.

The system control unit 44 may be constituted of one of the various processors, or may be constituted of a combination (for example, a combination of a plurality of FPGAs or a combination of a CPU and an FPGA) of two or more processors of the same type or different types.

Figure 3:
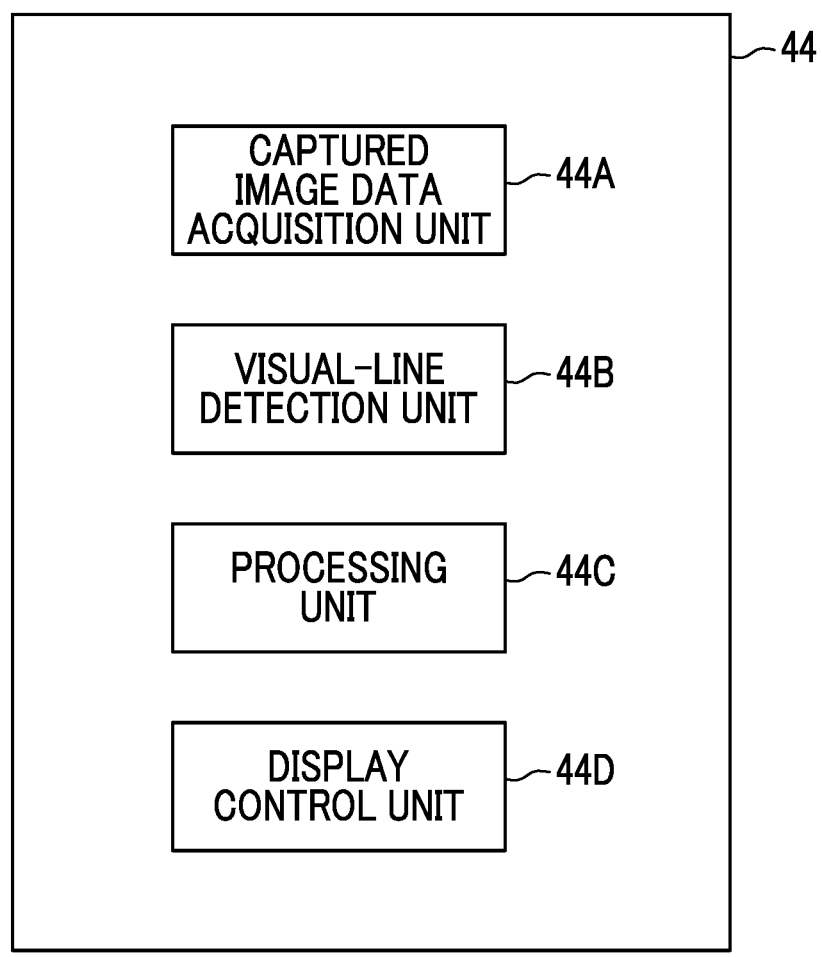
FIG. 3 is a view illustrating functional blocks of a system control unit 44 of a control device 4 illustrated in FIG. 2.

FIG. 3 is a view illustrating functional blocks of the system control unit 44 of the control device 4 illustrated in FIG. 2.

The processor of the system control unit 44 executes an inspection support program stored in the ROM built in the system control unit 44, thereby functioning as an inspection support device comprising a captured image data acquisition unit 44A, a visual-line detection unit 44B, a processing unit 44C, and a display control unit 44D.

The captured image data acquisition unit 44A sequentially acquires the captured image data obtained by processing the imaging signals, which are obtained by imaging the inside of the subject by the imaging element 23, by the signal processing unit 42.

The visual-line detection unit 44B acquires the visual line detection image data transmitted from the imaging device 8, and detects the visual line of the observer (an operator of the endoscope 1) directed to the display device 7 on the basis of images of both eyes of a person included in the visual line detection image data. The visual-line detection unit 44B outputs information of coordinates at which visual lines intersect each other on the display surface of the display device 7, as a visual line detection result.

The processing unit 44C performs recognition processing, which is the processing for detecting the lesion site from the captured image data and identifying the detected lesion site, on the captured image data acquired by the captured image data acquisition unit 44A. In the recognition processing, processing for detecting the lesion site is referred to as detection processing, and processing for identifying the lesion site is referred to as identification processing.

The detection of the lesion site refers to finding a site suspected of a lesion, such as a malignant tumor or a benign tumor (lesion candidate region), from the captured image data.

The identification of the lesion site refers to identifying the type, nature, or the like of the detected lesion site, such as whether or not the lesion site detected by the detection processing is malignant or benign, what kind of disease if malignant, or how much the degree of progress of the disease is.

The above detection processing and identification processing are performed by an image recognition model (for example, a neural network, a support vector machine, or the like) having a hierarchical structure and a parameter for extracting a feature amount determined by machine learning, deep learning, or the like.

The processing unit 44C controls the content of the above-described recognition processing performed on the captured image data, on the basis of the visual line detected by the visual-line detection unit 44B.

The display control unit 44D issues a command to the display controller 43 to perform the control of causing the display device 7 to display the captured image based on the captured image data recorded on the recording medium 45 as a live view image, and the control of causing the display device 7 to display the result of the above recognition processing by the processing unit 44C.

Figure 4:
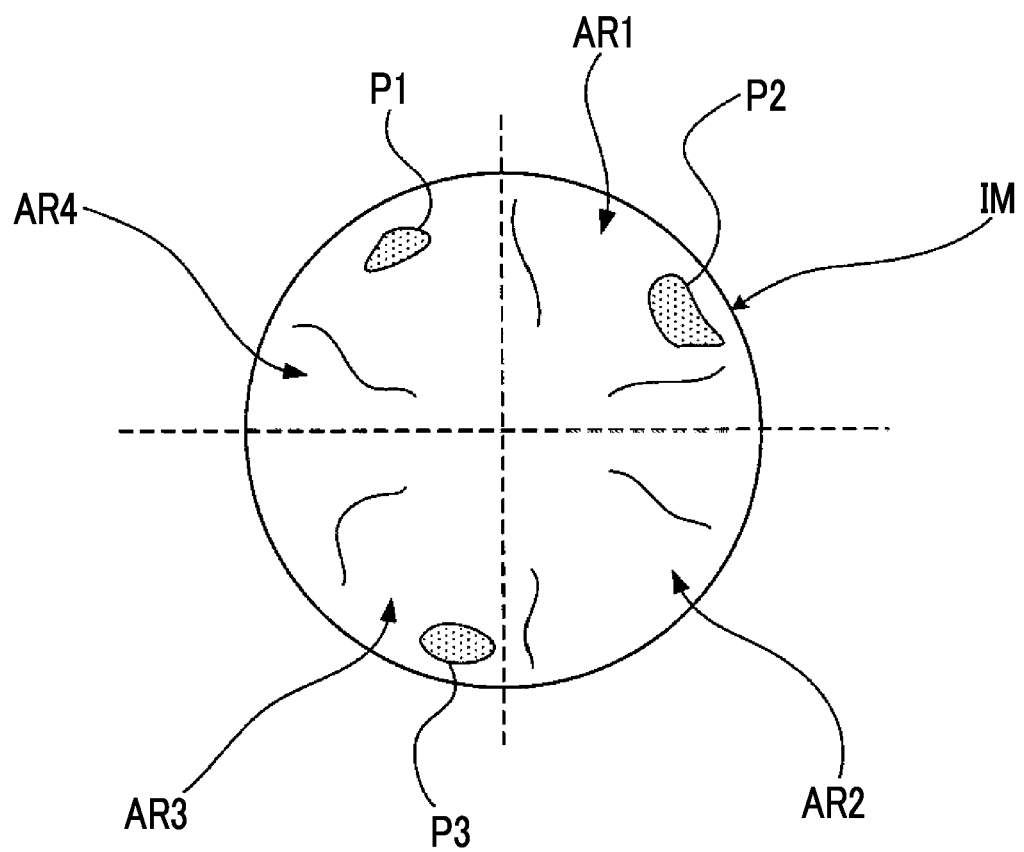
FIG. 4 is a view for explaining the operation of a processing unit 44C in the system control unit 44 illustrated in FIG. 3.

FIG. 4 is a view for explaining the operation of the processing unit 44C in the system control unit 44 illustrated in FIG. 3. FIG. 4 illustrates the captured image data IM acquired by the captured image data acquisition unit 44A. The captured image data IM illustrated in FIG. 4 includes lesion sites P1 to P3.

The processing unit 44C determines a region (hereinafter, referred to as an attention region) to which an attention is paid on the captured image data IM acquired by the captured image data acquisition unit 44A from the information on the coordinates of the display pixels intersecting with the operator's visual line on the display surface of the display device 7 output from the visual-line detection unit 44B.

For example, as illustrated in FIG. 4, the processing unit 44C divides the captured image data IM into a total of four regions including a divided region AR1, a divided region AR2, a divided region AR3, and a divided region AR4.

The processing unit 44C repeatedly performs the processing of specifying the pixel data of the captured image data IM corresponding to the coordinates from the coordinates of the display pixels output from the visual-line detection unit 44B for a fixed period. Then, the processing unit 44C determines, as the attention region, a divided region including the largest amount of pixel data specified during this fixed period among the divided regions AR1 to AR4.

The processing unit 44C executes recognition processing using the above-described image recognition model only on the attention region of the captured image data IM determined in this way, and does not execute the above-described recognition processing on the region (hereinafter, referred to as a non-attention region) of the captured image data IM excluding the attention region.

In FIG. 4, a case where the divided region AR4 is determined as the attention region is taken as an example. In this case, the pixel data in the divided region AR4 is input to the image recognition model and the recognition processing is executed, and the recognition processing is not performed on the pixel data in the divided regions AR1 to AR3.

In a case where the pixel data in the divided region AR4 is input to the image recognition model and the recognition processing is performed, the recognition processing allows the lesion site P1 included in the divided region AR4 to be detected and further allows the lesion site P1 to be identified.

Figure 5:
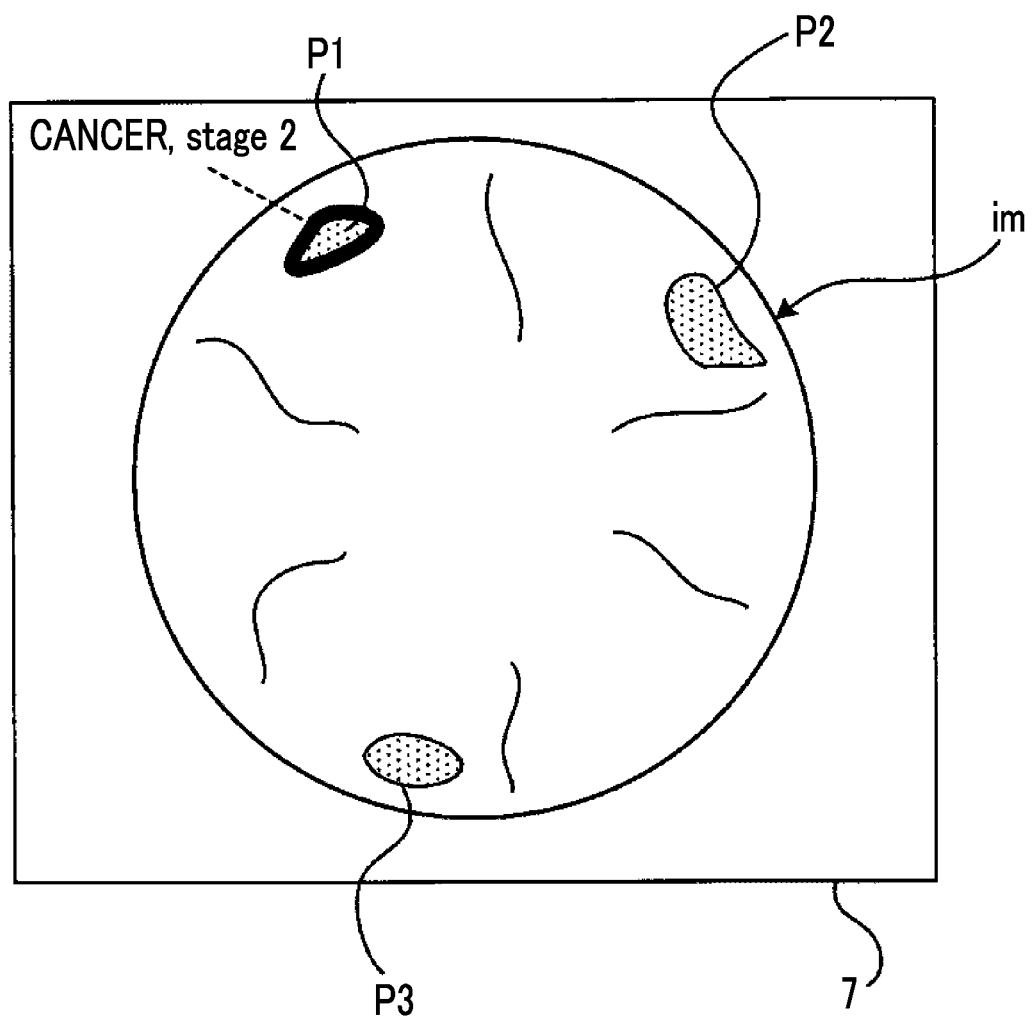
FIG. 5 is a view illustrating an example of an image displayed on a display device 7 under the control of a display control unit 44D in a system control unit 44 illustrated in FIG. 3.

In a case where the processing unit 44C detects the lesion site P1 and obtains the identification result of the lesion site P1, as illustrated in FIG. 5, the display control unit 44D causes the portion of the lesion site P1 to be displayed in a highlighted manner (highlighted by being enclosed in a thick frame in the example of FIG. 5) in a captured image im based on the captured image data IM, and causes the identification result (in the example of FIG. 5, the text of "cancer, stage 2") to be displayed together with the captured image im.

On the other hand, no recognition processing is performed on the divided regions AR1 to AR3. For that reason, as illustrated in FIG. 5, the lesion sites P2 and P3 are not displayed in a highlighted manner or the identification result is not displayed.

In this way, the processing unit 44C determines which region of the captured image data should be subjected to the recognition processing on the basis of the visual line detected by the visual-line detection unit 44B.

The operation of the endoscope device 100 configured as described above will be described with reference to a flowchart.

Figure 6:
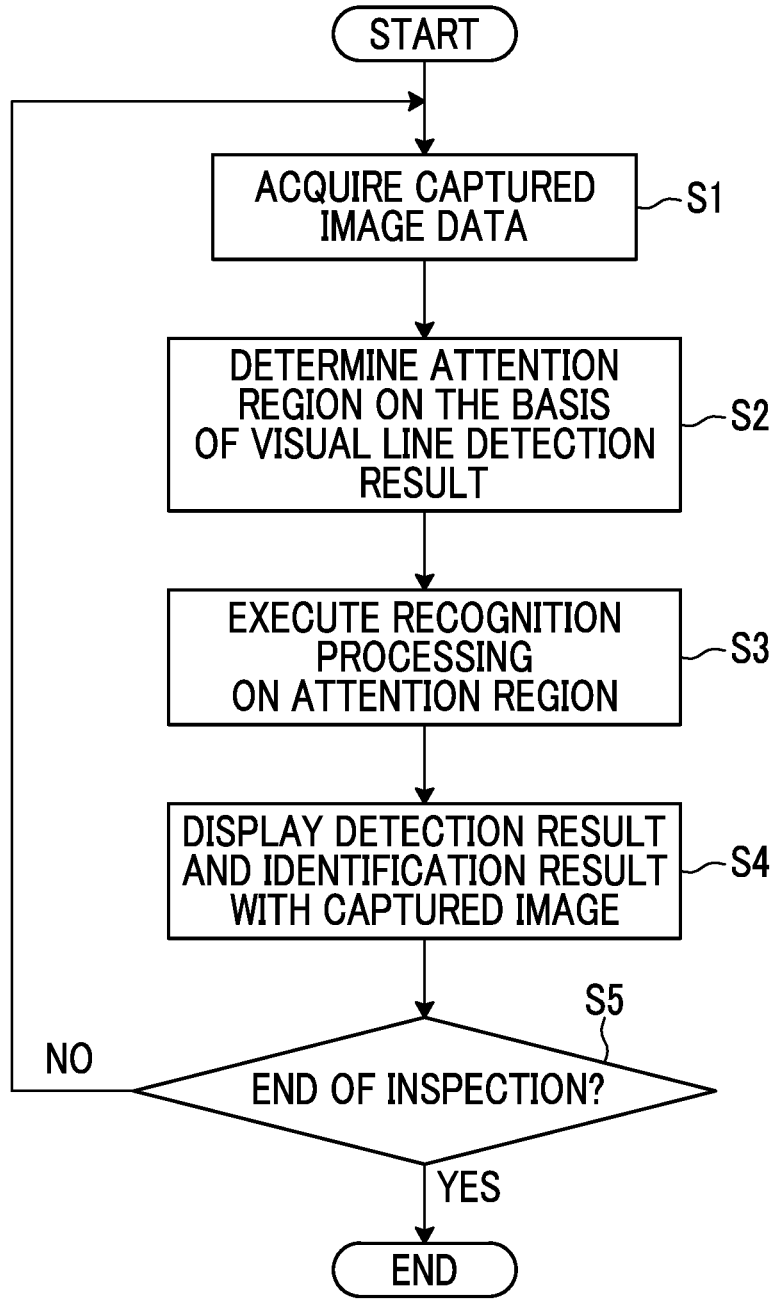
FIG. 6 is a flowchart for explaining the operation of the system control unit 44 illustrated in FIG. 4.

FIG. 6 is a flowchart for explaining the operation of the system control unit 44 illustrated in FIG. 4.

In a case where the capturing of the moving image by the imaging element 23 is started by the operation of the operating part 11, the captured image signals are output from the imaging element 23, the captured image signals are processed, and the captured image data for one frame of the moving image is sequentially generated and recorded on the recording medium 45. Additionally, captured images based on the generated captured image data are sequentially displayed as live view images on the display device 7. Moreover, the visual-line detection unit 44B starts the processing of detecting the visual line of the operator.

In a case where the capturing of the moving image is started, the captured image data acquisition unit 44A acquires the captured image data generated by the signal processing unit 42 (Step S1).

Next, the processing unit 44C determines the attention region in the captured image data acquired in Step S1, on the basis of the operator's visual line detected by the visual-line detection unit 44B (Step S2).

Next, the processing unit 44C executes the above-described recognition processing (detection processing and identification processing) only on the determined attention region (Step S3).

In a case where the recognition processing in Step S3 is completed, the detection result, which is the result of the detection processing, and the identification result, which is the result of the identification processing, are displayed on the display device 7 together with the captured image as exemplified in FIG. 5 (Step S4) by the control of the display control unit 44D.

After Step S4, in a case where an instruction to end imaging by the imaging element 23 is performed and the inspection is ended (Step S5: YES), the system control unit 44 ends the processing. On the other hand, in a case where the inspection is continued (Step S5: NO), the processing returns to Step S1, and the subsequent processing is repeated.

As described above, according to the endoscope device 100, the recognition processing is performed only on the attention region where the visual line of the operator who operates the endoscope 1 is gathered. Even in a situation where both hands are closed, the operator can obtain the detection result and the identification result in the site to which an attention is paid simply by changing the position where the visual line is directed to the captured image, and can perform the inspection efficiently and accurately.

Additionally, according to the endoscope device 100, the range where the recognition processing is performed can be narrowed. For this reason, the processing load on the system control unit 44 can be reduced in a case where the detection of a lesion site and the identification of the lesion site are performed in real time during the endoscopy. In this way, since the processing load can be reduced, a model having higher detection accuracy or identification accuracy of the lesion site can be used as the image recognition model used for the recognition processing, and the accuracy of the endoscopy can be improved.

Figure 7:
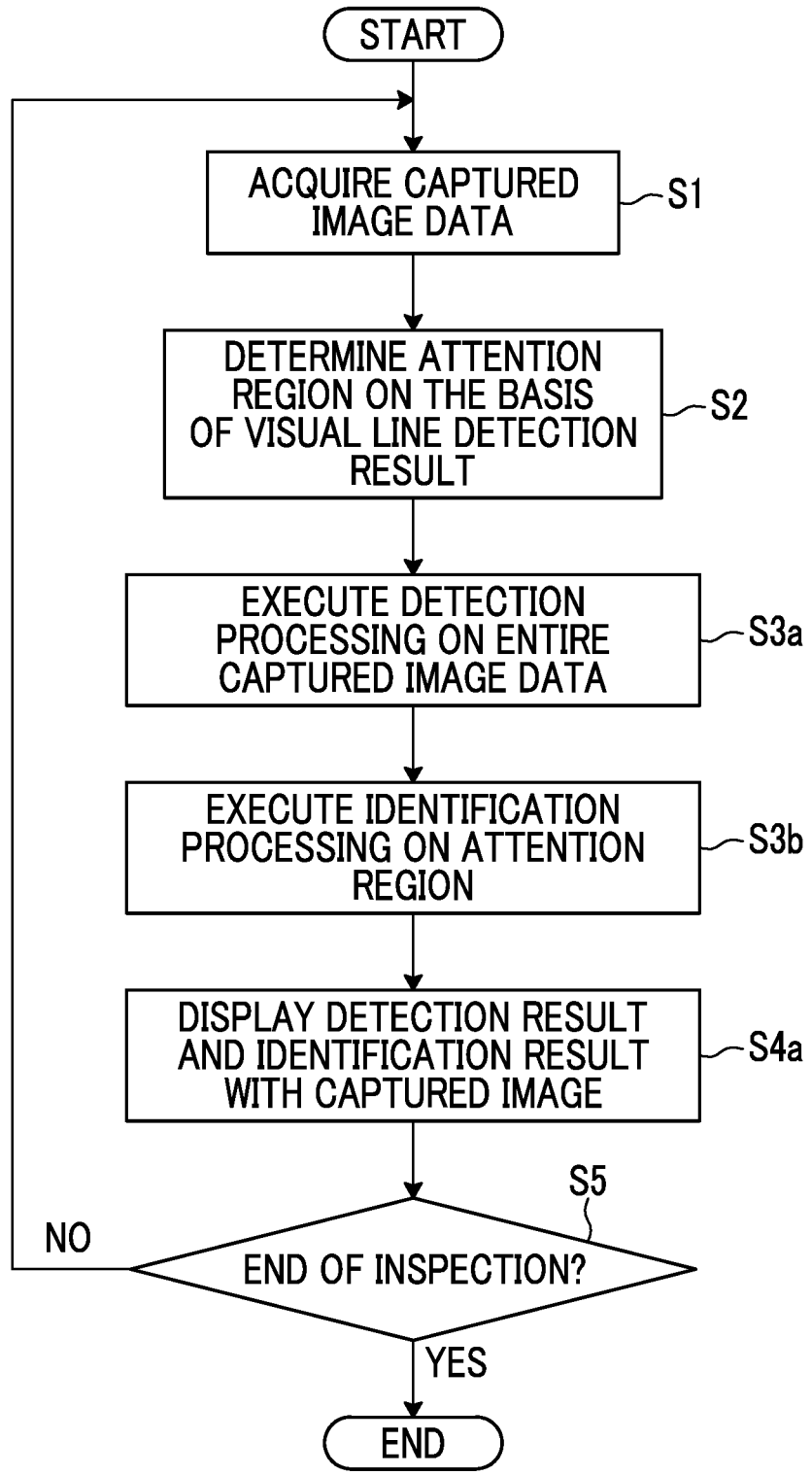
FIG. 7 is a flowchart for explaining a first modification example of the operation of the system control unit 44 illustrated in FIG. 4.

FIG. 7 is a flowchart for explaining a first modification example of the operation of the system control unit 44 illustrated in FIG. 4.

The flowchart illustrated in FIG. 7 is the same as FIG. 6 except that Step S3 is changed to Steps S3a and S3b and Step S4 is changed to Step S4a. In FIG. 7, the same processing as that in FIG. 6 is denoted by the same reference numerals, and the description thereof will be omitted.

In a case where the attention region is determined in Step S2, the processing unit 44C performs the detection processing using the same image recognition model on each of the attention region in the captured image data and the non-attention region that is a region excluding the attention region, and detects a lesion site. That is, in Step S3a, the detection processing of the lesion site is performed on the entire captured image data (Step S3a).

After the lesion site is detected by the processing of Step S3a, the processing unit 44C performs the identification processing only on the attention region determined in Step S2 (Step S3b).

After Step S3b, the display control unit 44D causes the display device 7 to display the result of the detection processing in Step S3a and the result of the identification processing in Step S3b together with the captured image (Step S4a). After Step S4a, the processing proceeds to Step S5.

Figure 8:
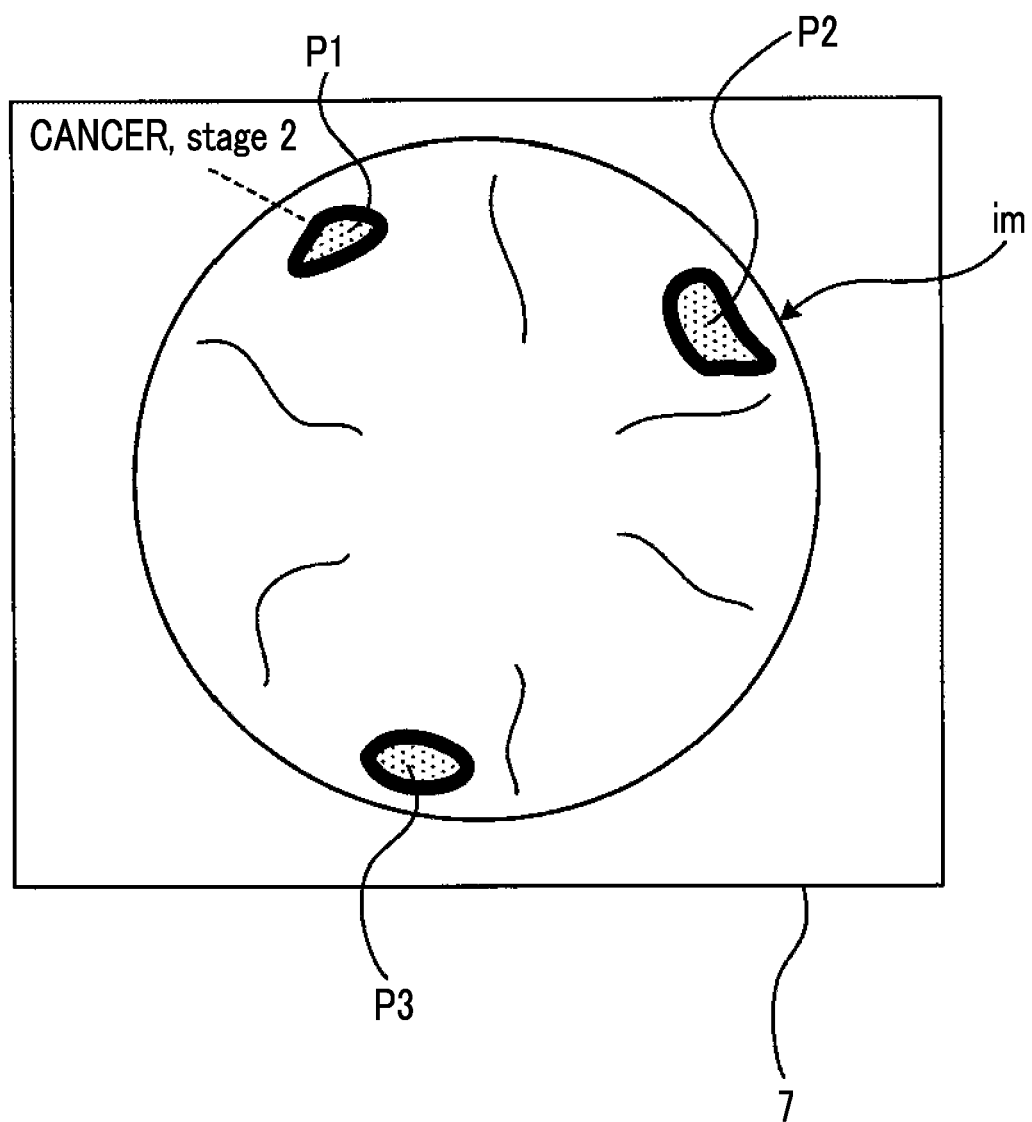
FIG. 8 is a view illustrating an example of an image displayed on the display device 7 in Step S4a illustrated in FIG. 7.

FIG. 8 is a view illustrating an example of an image displayed on the display device 7 in Step S4a illustrated in FIG. 7. As illustrated in FIG. 8, the lesion sites P1 to P3 on the captured image im are displayed in a highlighted manner as the detection result of the lesion site. Then, the identification result is displayed only for the lesion site P1 to which the operator's visual line is directed.

In this way, in the first modification example illustrated in FIG. 7, the processing unit 44C of the system control unit 44 performs the detection processing on the entire captured image data, and performs the identification processing only on the attention region.

In this way, in the region to which an attention is paid by the operator, the location of the lesion site and the identification result of the lesion site are displayed. Therefore, this can be used for the determination of the subsequent treatment.

Additionally, even in a region to which an attention is not paid by the operator, a lesion site is clearly specified in a case where the lesion site is present. For this reason, the possibility that the lesion site is overlooked can be reduced, and the accuracy of the inspection can be improved.

Additionally, since the identification processing is performed only on the attention region, the processing load on the system control unit 44 can be reduced, and the inspection accuracy can be improved by adopting highly accurate identification processing.

In the first modification example, in the state illustrated in FIG. 8, for example, in a case where the operator wants to know the identification result of the lesion site P2, the operator directs his/her visual line from the lesion site P1 to the lesion site P2, thereby allowing the identification result to be displayed. In this way, the identification result is displayed only when necessary, so that the inspection can be efficiently performed.

Figure 9:
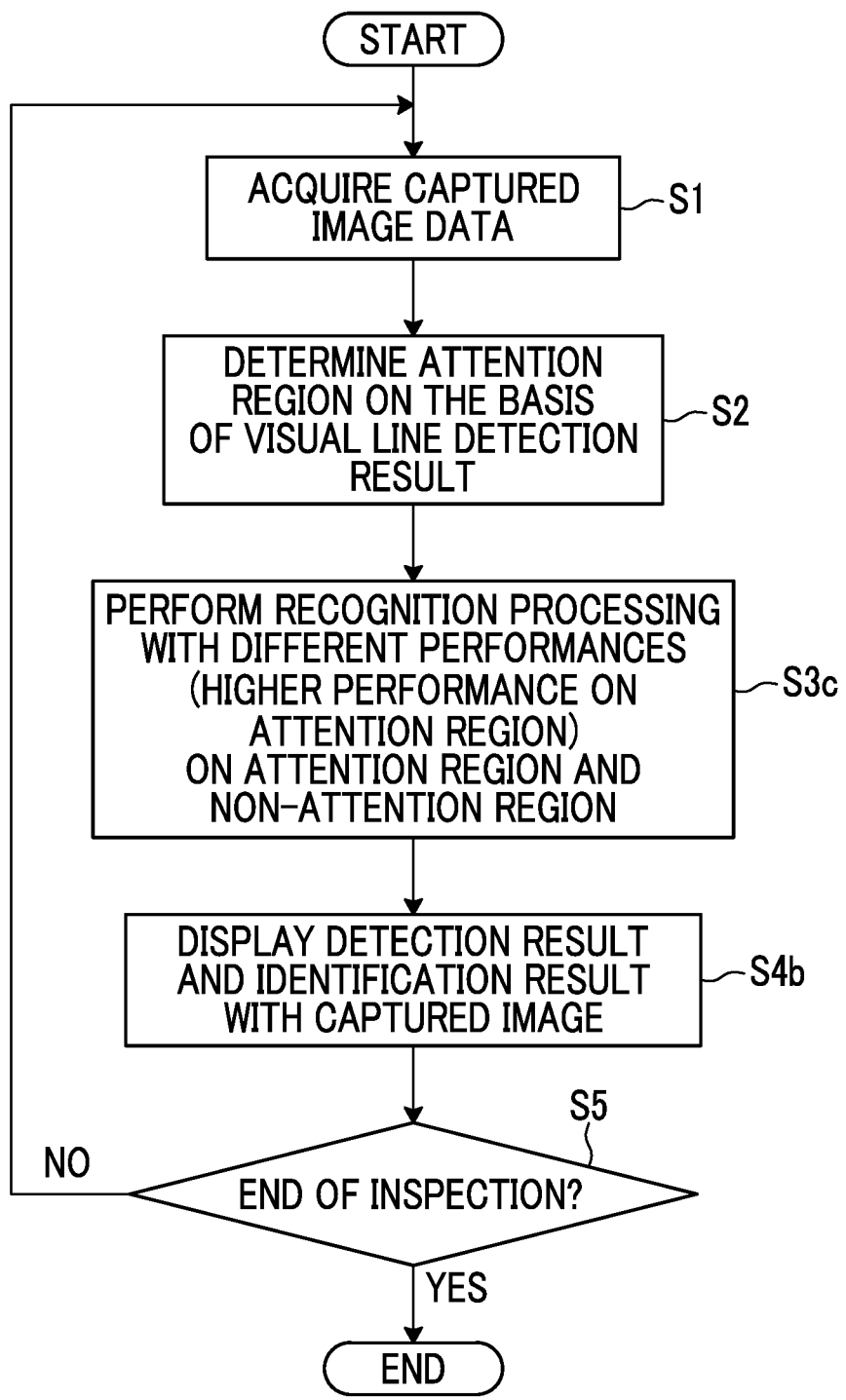
FIG. 9 is a flowchart for explaining a second modification example of the operation of the system control unit 44 illustrated in FIG. 4.

FIG. 9 is a flowchart for explaining a second modification example of the operation of the system control unit 44 illustrated in FIG. 4.

The flowchart illustrated in FIG. 9 is the same as that in FIG. 6 except that Step S3 is changed to Step S3c and Step S4 is changed to Step S4b. In FIG. 9, the same processing as that in FIG. 6 is denoted by the same reference numerals, and the description thereof will be omitted.

In a case where the attention region is determined in Step S2, the processing unit 44C performs the recognition processing with different performances on the attention region in the captured image data and the non-attention region that is a region excluding the attention region (Step S3c).

That is, in Step S3c, the processing unit 44C makes the content of the recognition processing (at least one of the configuration or the parameters of the image recognition model) different between the attention region and the non-attention region of the captured image data.

Specifically, the processing unit 44C controls the content of the recognition processing on the attention region such that the performance of the recognition processing is higher than the performance of the recognition processing on the non-attention region.

For example, in the case of detection processing, the higher the resolution of image data that can be analyzed by the image recognition model, the higher the performance of the detection processing. Alternatively, the greater the number of layers of the image recognition model, the higher the performance of the detection processing.

Additionally, in the case of the identification processing, the performance of the identification processing is higher as the type of information that can be output as a result by the image recognition model is more. Alternatively, the higher the number of layers of the image recognition model, the higher the performance of the identification processing.

Alternatively, the higher the resolution of the image data that can be analyzed by the image recognition model, the higher the performance of the identification processing.

After Step S3c, the display control unit 44D causes the display device 7 to display the result of the recognition processing in Step S3c together with the captured image (Step S4b). After Step S4b, the processing proceeds to Step S5.

Figure 10:
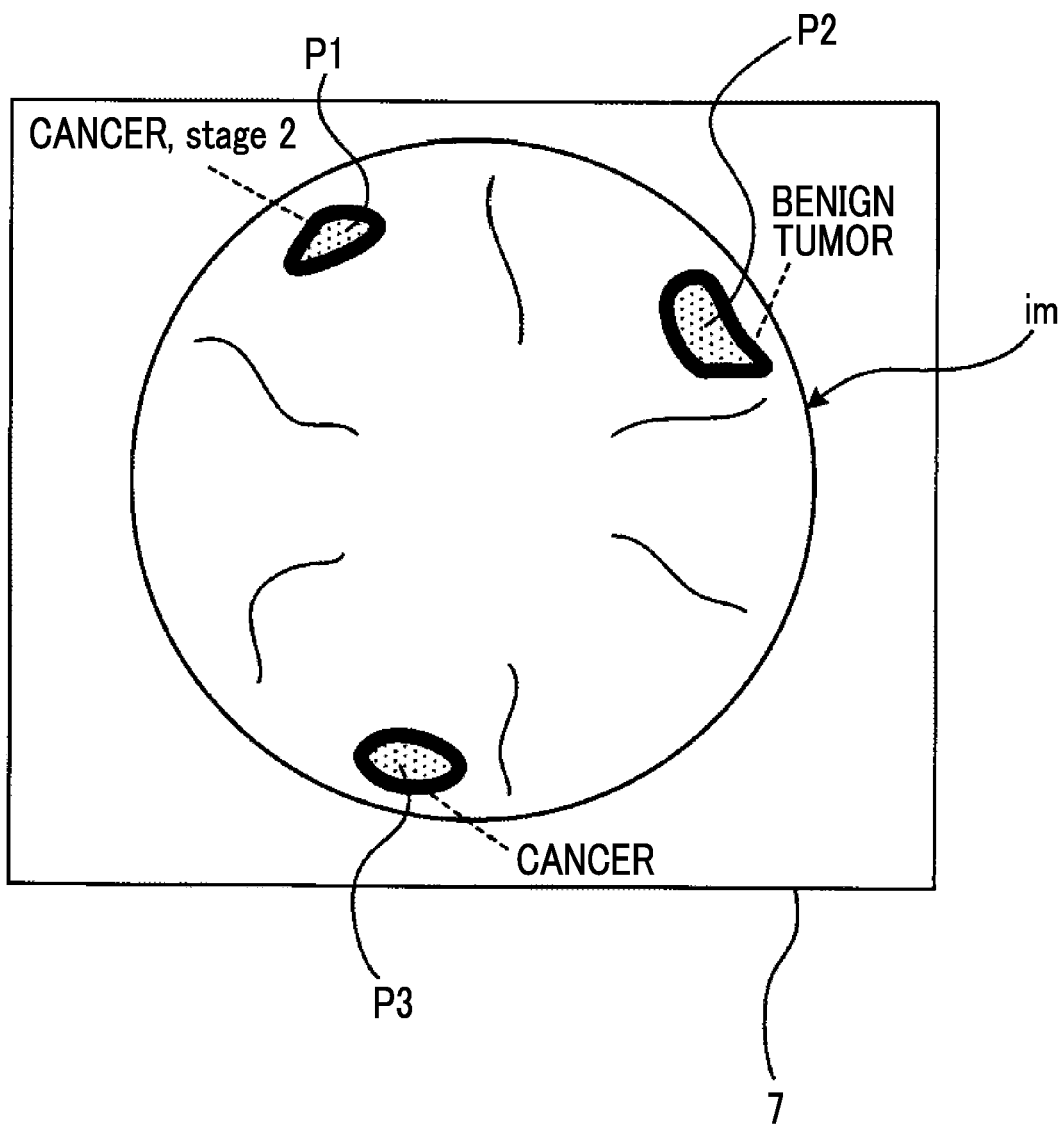
FIG. 10 is a view illustrating an example of an image displayed on the display device 7 in Step S4b illustrated in FIG. 9.

FIG. 10 is a view illustrating an example of an image displayed on the display device 7 in Step S4b illustrated in FIG. 9.

As illustrated in FIG. 10, the lesion sites P1 to P3 on the captured image are displayed in a highlighted manner as detection results thereof. Also, for the lesion site P1 to which the operator's visual line is directed, information on the stage of the cancer is displayed in addition to the type (cancer) of tumor as the identification result. On the other hand, for the lesion sites P2 and P3 to which the operator's visual line is not directed, only the type of tumor is displayed.

In this way, the recognition processing with relatively high performance is performed on the region of the captured image to which the operator's visual line is directed, so that the inspection can be efficiently advanced. Additionally, the recognition processing with relatively low performance is performed even on a region of the captured image to which the operator's visual line is not directed, so that a lesion site can be prevented from being overlooked and the inspection efficiency can be improved.

Figure 11:
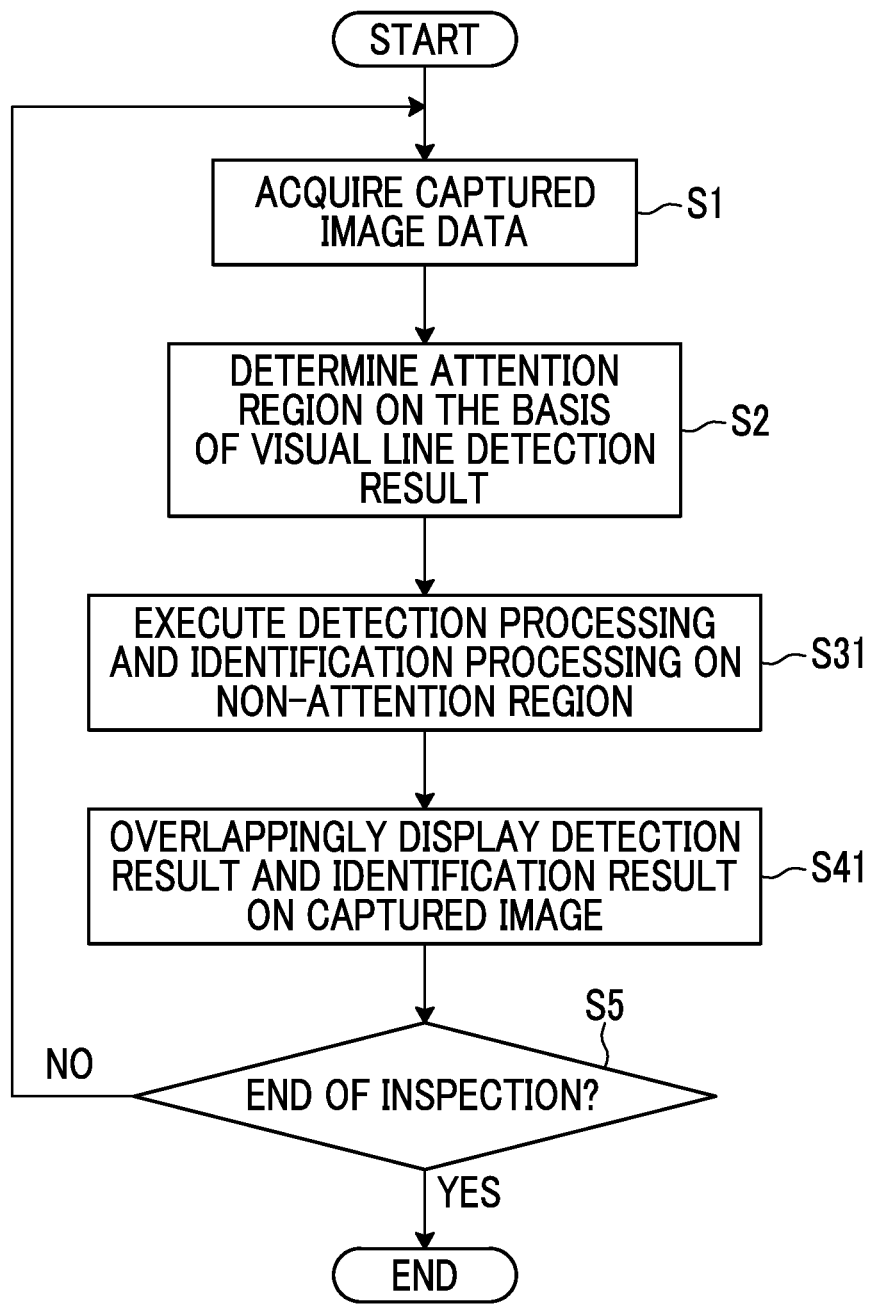
FIG. 11 is a flowchart for explaining a third modification example of the operation of the system control unit 44 illustrated in FIG. 4.

FIG. 11 is a flowchart for explaining a third modification example of the operation of the system control unit 44 illustrated in FIG. 4.

The flowchart illustrated in FIG. 11 is the same as that in FIG. 6 except that Step S3 is changed to Step S31 and Step S4 is changed to Step S41. In FIG. 11, the same processing as that in FIG. 6 is denoted by the same reference numerals, and the description thereof will be omitted.

In a case where the attention region is determined in Step S2, the processing unit 44C performs the identification processing only on the non-attention region which is a region excluding the attention region in the captured image data (Step S31).

After Step S31, the display control unit 44D causes the display device 7 to display the result of the recognition processing in Step S31 together with the captured image (Step S41). After Step S41, the processing proceeds to Step S5.

In the third modification example, the recognition processing is performed only on a region of the captured image to which an attention is not paid by the operator, and the result is displayed. Operators are often skilled physicians. For this reason, regarding the region of the captured image visually observed by the operator, it can be considered that the detection of the lesion and the identification of the lesion are performed with high accuracy through the experience of the operator.

Thus, as in the third modification example, the identification processing is performed only on the region where the visual line is not directed, so that a lesion site that cannot be detected through the operator's experience can be prevented from being overlooked and the accuracy of the inspection can be enhanced. Additionally, according to the third modification example, a range in which the identification processing is performed is narrowed. Therefore, the accuracy of the identification processing can be increased, and the processing load on the system control unit 44 can be reduced.

Figure 12:
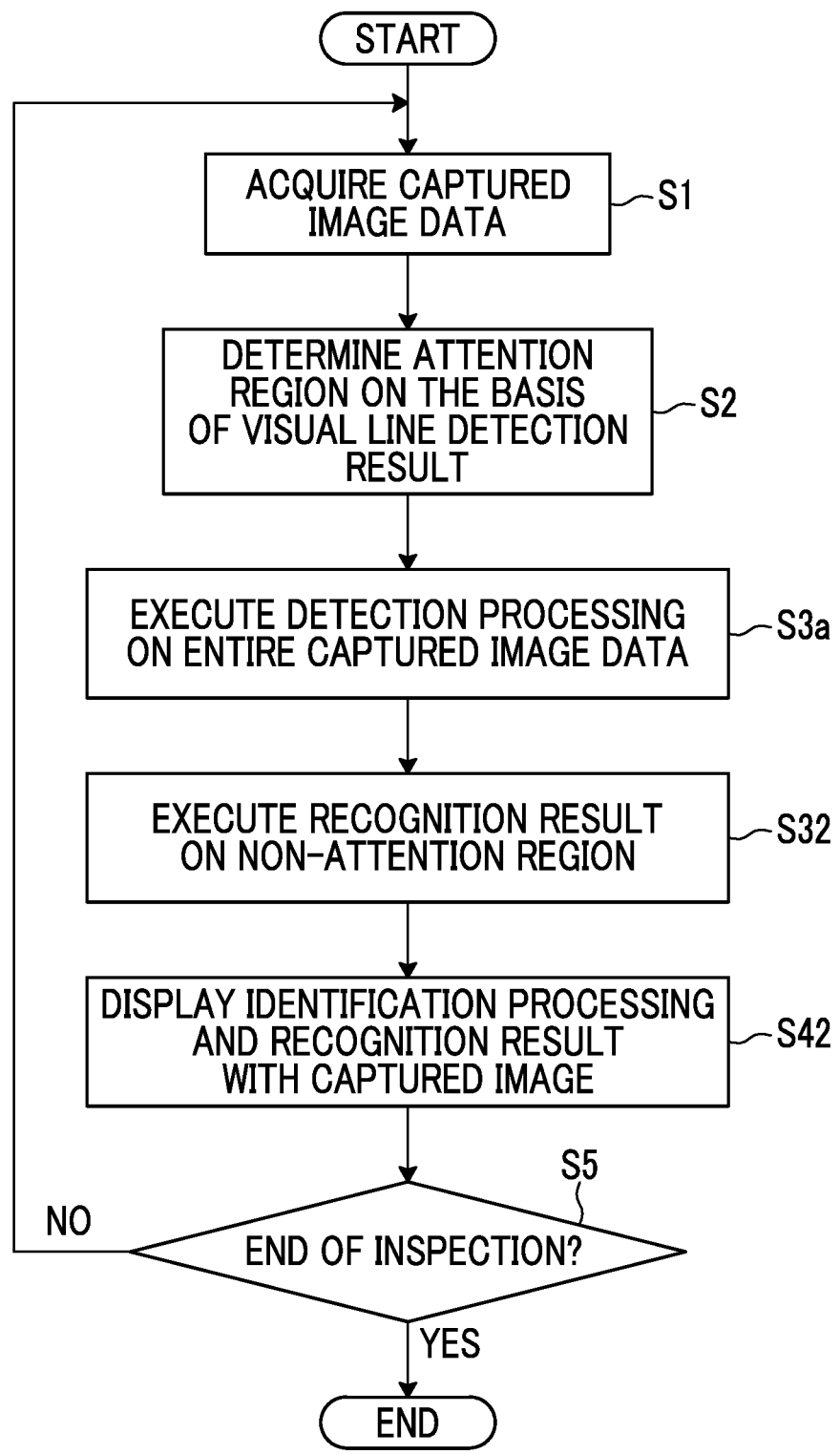
FIG. 12 is a flowchart for explaining a fourth modification example of the operation of the system control unit 44 illustrated in FIG. 4.

FIG. 12 is a flowchart for explaining a fourth modification example of the operation of the system control unit 44 illustrated in FIG. 4.

The flowchart illustrated in FIG. 12 is the same as that in FIG. 7 except that Step S3b is changed to Step S32 and Step S4a is changed to Step S42. In FIG. 12, the same processing as that in FIG. 7 is denoted by the same reference numerals, and the description thereof will be omitted.

After the lesion site is detected by the processing in Step S3a, the processing unit 44C performs the identification processing only on the non-attention region that is a region excluding the attention region determined in Step S2 (Step S32).

After Step S32, the display control unit 44D causes the display device 7 to display the result of the detection processing in Step S3a and the result of the identification processing in Step S32 together with the captured image (Step S42).

According to the fourth modification example, in a region to which an attention is not paid by the operator, the location of the lesion site and the identification result of the lesion site are displayed. For this reason, this can be used for the determination of the subsequent treatment.

Additionally, even in the region to which an attention is paid by the operator, a lesion site can be clearly specified in a case where the lesion site is present. For this reason, the possibility that the lesion site is overlooked can be reduced, and the accuracy of the inspection can be improved.

Additionally, since the identification processing is performed only on the non-attention region, the processing load on the system control unit 44 can be reduced, and the inspection accuracy can be improved by adopting highly accurate identification processing.

Figure 13:
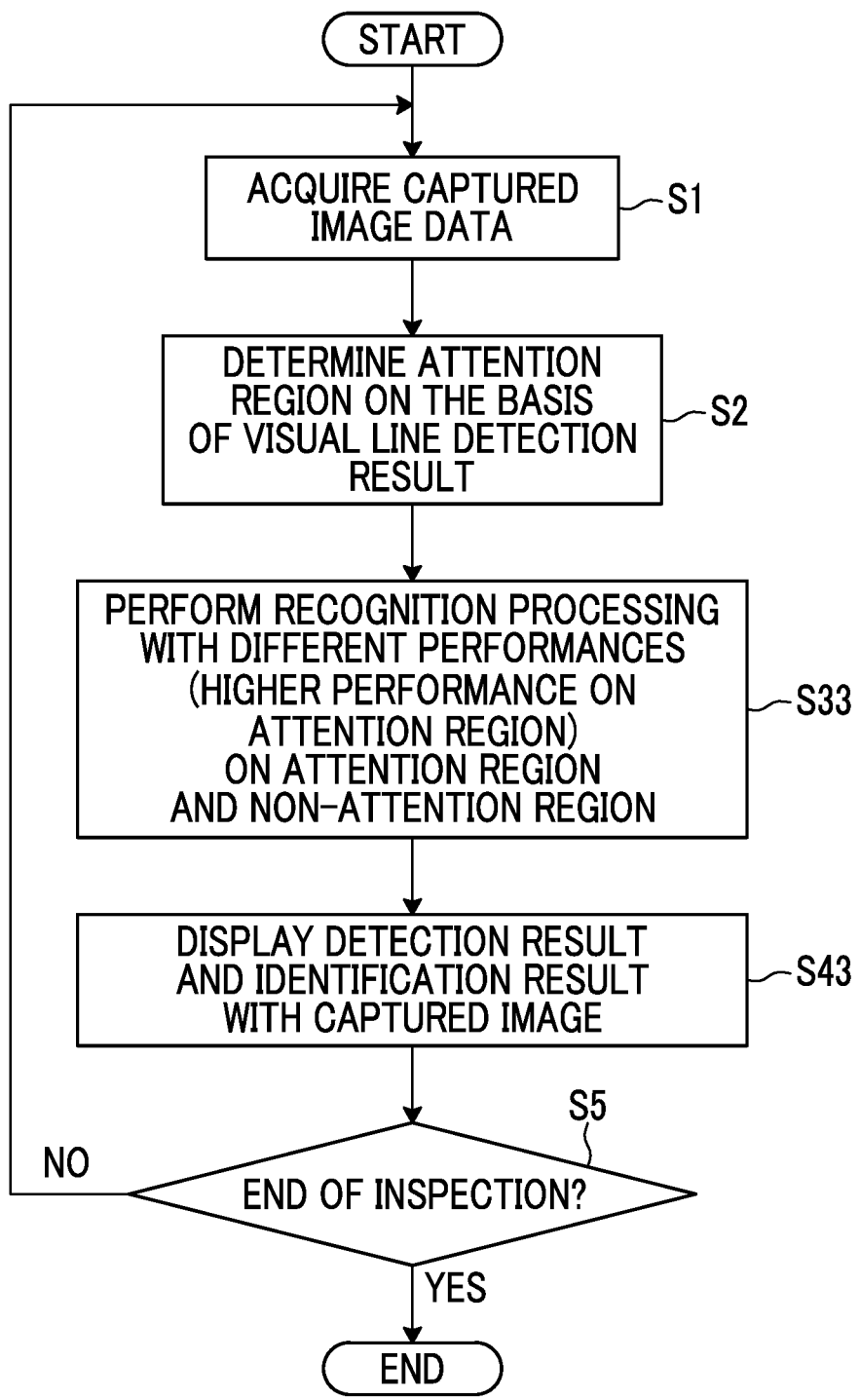
FIG. 13 is a flowchart for explaining a fifth modification example of the operation of the system control unit 44 illustrated in FIG. 4.

FIG. 13 is a flowchart for explaining a fifth modification example of the operation of the system control unit 44 illustrated in FIG. 4.

The flowchart illustrated in FIG. 13 is the same as that in FIG. 9 except that Step S3c is changed to Step S33 and Step S4b is changed to Step S43. In FIG. 13, the same processing as that in FIG. 9 is denoted by the same reference numerals, and the description thereof will be omitted.

In a case where the attention region is determined in Step S2, the processing unit 44C performs the recognition processing with different performances on the attention region in the captured image data and the non-attention region that is a region excluding the attention region (Step S33).

That is, in Step S33, the processing unit 44C makes the content of the recognition processing (at least one of the configuration or the parameters of the image recognition model) different between the attention region and the non-attention region of the captured image data.

Specifically, the processing unit 44C controls the content of the recognition processing on the attention region such that the performance of the recognition processing is higher than the performance of the recognition processing on the non-attention region.

After Step S33, the display control unit 44D causes the display device 7 to display the result of the recognition processing in Step S33 together with the captured image (Step S43). After Step S43, the processing proceeds to Step S5.

According to the fifth modification example, the recognition processing with relatively high performance is performed on a region of the captured image to which the operator's visual line is not directed. Therefore, a lesion site can be efficiently prevented from being overlooked, and the inspection can be efficiently performed. Additionally, the recognition processing with relatively low performance is performed even on a region of the captured image to which the operator's visual line is directed, so that a lesion site can be prevented from being overlooked and the inspection efficiency can be improved.

In configurations other than the modification examples described with reference to FIGS. 7 and 12, the identification processing is not essential as the recognition processing performed by the processing unit 44C. Even in a case where the processing unit 44C performs only the detection processing, it is possible to obtain the effects of reducing the processing load on the system control unit 44, improving the accuracy of the detection processing, improving the inspection efficiency, and the like.

In the above description, the visual line of the operator is detected on the basis of the image data obtained by imaging the subject with the imaging device 8. However, the method of detecting the visual line is not limited to this, and various well-known methods can be adopted. For example, the visual line can be detected on the basis of the detection information of an acceleration sensor mounted on a glasses-type wearable terminal worn by the operator.

As described above, the following matters are disclosed in the present specification.

(1) An inspection support device comprising a captured image data acquisition unit that acquires captured image data obtained by imaging the inside of a subject with an endoscope; a visual-line detection unit that detects a visual line directed to a display device that displays a captured image based on the captured image data; a processing unit that performs processing for performing at least detection of the detection of a lesion site from the captured image data and identification of the detected lesion site on the captured image data; and a display control unit that causes the display device to display a result of the processing by the processing unit, wherein the processing unit controls a content of the processing on the captured image data on the basis of the visual line detected by the visual-line detection unit.

(2) The inspection support device according to (1), wherein the processing unit determines an attention region to which an attention is paid in the captured image data on the basis of the visual line detected by the visual-line detection unit, does not execute the processing only on the attention region, and executes the processing only on a non-attention region that is a region excluding the attention region in the captured image data.

(3) The inspection support device according to (1), wherein the processing unit performs the processing for detecting the lesion site on the entire captured image data, determine an attention region to which an attention is paid in the captured image data on the basis of the visual line detected by the visual-line detection unit, and performs the processing for identifying the lesion site only on the attention region.

(4) The inspection support device according to (1), wherein the processing unit determines an attention region to which an attention is paid in the captured image data on the basis of the visual line detected by the visual-line detection unit, executes the processing on the entire captured image data, and makes a content of the processing on the attention region in the captured image data different from a content of the processing on a non-attention region, which is a region excluding the attention region in the captured image data.

(5) The inspection support device according to (4), wherein the processing unit controls the content of the processing on the attention region such that performance of the processing is higher than performance of the processing on the non-attention region.

(6) The inspection support device according to (1), wherein the processing unit determines an attention region to which an attention is paid in the captured image data on the basis of the visual line detected by the visual-line detection unit, does not execute the processing on the attention region, and executes the processing only on a non-attention region that is a region excluding the attention region in the captured image data.

(7) The inspection support device according to (1), wherein the processing unit determines an attention region to which an attention is paid in the captured image data on the basis of the visual line detected by the visual-line detection unit, and performs the processing for detecting the lesion site on the entire captured image data, and executes the processing for identifying the lesion site only on a non-attention region that is a region excluding the attention region in the captured image data.

(8) The inspection support device according to (4), wherein the processing unit controls the content of the processing on the non-attention region such that performance of the processing is higher than performance of the processing on the attention region.

(9) An endoscope device comprising: the inspection support device according to any one of (1) to (8); and the endoscope.

(10) An inspection support method comprising: a captured image data acquisition step of acquiring captured image data obtained by imaging the inside of a subject with an endoscope; a visual-line detection step of detecting a visual line directed to a display device that displays a captured image based on the captured image data; a processing step of performing processing for performing at least a detection of a lesion site from the captured image data out of the detection of the lesion site and identification of the detected lesion site on the captured image data; and a display control step of causing the display device to display a result of the processing by the processing step, wherein in the processing step, a content of the processing on the captured image data is controlled on the basis of the visual line detected by the visual-line detection step.

(11) An inspection support program for causing a computer execute a captured image data acquisition step of acquiring captured image data obtained by imaging the inside of a subject with an endoscope; a visual-line detection step of detecting a visual line directed to a display device that displays a captured image based on the captured image data; a processing step of performing processing for performing at least a detection of a lesion site from the captured image data out of the detection of the lesion site and identification of the detected lesion site on the captured image data; and a display control step of causing the display device to display a result of the processing by the processing step, wherein in the processing step, a content of the processing on the captured image data is controlled on the basis of the visual line detected by the visual-line detection step.

According to the invention, it is possible to provide the inspection support device, the endoscope device, the inspection support method, and the inspection support program that can make both the accuracy and efficiency of the inspection using the endoscope compatible.

EXPLANATION OF REFERENCES

100: endoscope device
1: endoscope

2: body part
10: insertion part
10A: flexible part
10B: bending part
10C: distal end part
11: operating Part
12: angle knob
13: universal cord
13A, 13B: connector part
6: input unit
7: display device
8: imaging device
21: objective lens
Ax: optical axis
22: lens group
23: imaging element
24: ADC
25: memory
26: communication interface
27: imaging control unit
4: control device
41: communication interface
42: signal processing unit
43: display controller
44: system control unit
44A: captured image data acquisition unit
44B: visual-line detection unit
44C: processing unit
44D: display control unit
45: recording medium
5: light source device
50: illumination lens
51: light source control unit
52: light source unit
53: light guide
IM: captured image data
im: captured image
AR1, AR2, AR3, AR4: divided region
P1, P2, P3: lesion site

What is claimed is:

1. An inspection support device comprising:
a processor configured to
acquire captured image data obtained by imaging the inside of a subject with an endoscope;
detect a visual line directed to a display device that displays a captured image based on the captured image data;
perform processing on the captured image data to detect a lesion site from the captured image data or to detect a lesion site from the captured image data and identify the detected lesion site; and
cause the display device to display a result of the processing on the captured image data by the processor,
wherein the processor determines an attention region to which an attention is paid in the captured image data on the basis of the visual line, and controls the processing on the attention region in the captured image data.

2. The inspection support device according to claim 1, wherein the processor does not execute the processing on a non-attention region that is a region excluding the attention region in the captured image data, and executes the processing only on the attention region.

3. The inspection support device according to claim 1, wherein the processor performs the processing to detect the lesion site on the entire captured image data and performs the processing to identify the lesion site only on the attention region.

4. The inspection support device according to claim 1, wherein the processor executes the processing on the entire captured image data, and makes a content of the processing on the attention region in the captured image data different from a content of the processing on a non-attention region, which is a region excluding the attention region in the captured image data.

5. The inspection support device according to claim 4, wherein the processor controls the processing such that performance of the processing on the attention region is higher than performance of the processing on the non-attention region.

6. The inspection support device according to claim 1, wherein the processor determines an attention region to which an attention is paid in the captured image data on the basis of the visual line detected by the processor, does not execute the processing on the attention region, and executes the processing only on a non-attention region that is a region excluding the attention region in the captured image data.

7. The inspection support device according to claim 1, wherein the processor determines an attention region to which an attention is paid in the captured image data on the basis of the visual line detected by the processor, and performs the processing to detect the lesion site on the entire captured image data, and executes the processing to identify the lesion site only on a non-attention region that is a region excluding the attention region in the captured image data.

8. The inspection support device according to claim 4, wherein the processor controls the processing such that performance of the processing on the non-attention region is higher than performance of the processing on the attention region.

9. An endoscope device comprising:
the inspection support device according to claim 1; and
the endoscope.

10. An endoscope device comprising:
the inspection support device according to claim 2; and
the endoscope.

11. An endoscope device comprising:
the inspection support device according to claim 3; and
the endoscope.

12. An endoscope device comprising:
the inspection support device according to claim 4; and
the endoscope.

13. An endoscope device comprising:
the inspection support device according to claim 5; and
the endoscope.

14. An endoscope device comprising:
the inspection support device according to claim 6; and
the endoscope.

15. An endoscope device comprising:
the inspection support device according to claim 7; and
the endoscope.

16. An endoscope device comprising:
the inspection support device according to claim 8; and
the endoscope.

17. An inspection support method comprising:
a captured image data acquisition step of acquiring captured image data obtained by imaging the inside of a subject with an endoscope;
a visual-line detection step of detecting a visual line directed to a display device that displays a captured image based on the captured image data;
a processing step of performing processing on the captured imaged data to detect a lesion site from the captured image data or to detect a lesion site from the captured image data and identify the detected lesion site; and a display control step of causing the display device to display a result of the processing on the captured image data by the processing step, wherein in the processing step, an attention region to which an attention is paid in the captured image data is determined on the basis of the visual line, and the processing on the captured image data is controlled to be performed in the attention region.

18. A non-transitory computer readable recording medium storing an inspection support program for causing a computer to execute a captured image data acquisition step of acquiring captured image data obtained by imaging the inside of a subject with an endoscope, a visual-line detection step of detecting a visual line directed to a display device that displays a captured image based on the captured image data, a processing step of performing processing on the captured image data to detect a lesion site from the captured image data or to detect a lesion site from the captured image data and identify the detected lesion site, and a display control step of causing the display device to display a result of the processing on the captured image data by the processing step, wherein in the processing step, an attention region to which an attention is paid in the captured image data is determined on the basis of the visual line, and the processing on the captured image data is controlled to be performed in the attention region.

* * * * *